US012762663B2

(12) United States Patent
Redford

(10) Patent No.: US 12,762,663 B2
(45) Date of Patent: Oct. 13, 2026

(54) NON-OCCLUDED DUAL LUMEN ENDOTRACHEAL TUBE

(71) Applicant: Lazzaro Medical, Inc., Boulder, CO (US)

(72) Inventor: Ryan Redford, Irvine, CA (US)

( * ) Notice: Subject to any disclaimer, the term of this patent is extended or adjusted under 35 U.S.C. 154(b) by 199 days.

(21) Appl. No.: 18/601,525

(22) Filed: Mar. 11, 2024

(65) Prior Publication Data

US 2024/0298886 A1 Sep. 12, 2024

Related U.S. Application Data

(60) Provisional application No. 63/451,477, filed on Mar. 10, 2023.

(51) Int. Cl.
*G06T 5/70* (2024.01)
*A61B 5/00* (2006.01)

(52) U.S. Cl.
CPC .............. *G06T 5/70* (2024.01); *A61B 5/0075* (2013.01)

(58) Field of Classification Search
CPC ................................ A61B 5/0075; G06T 5/70
See application file for complete search history.

(56) References Cited

U.S. PATENT DOCUMENTS 8,880,150 B2 11/2014 Mckenna et al.
10,980,955 B2 4/2021 Nawn et al.
11,471,027 B2 10/2022 Lin
2005/0113643 A1 5/2005 Hale et al.
2008/0309797 A1 12/2008 Neta
2010/0053312 A1 3/2010 Watanabe et al.
2010/0103250 A1 4/2010 Ishihara
2010/0147309 A1 6/2010 Cuevas et al.
2013/0253310 A1* 9/2013 McKenna .............. A61B 5/742 600/424
2015/0073210 A1 3/2015 Woods et al.
2015/0374210 A1 12/2015 Durr et al.
2019/0200906 A1 7/2019 Shelton, IV et al.
(Continued)

FOREIGN PATENT DOCUMENTS

WO WO2017214193 12/2017
WO WO2021226493 11/2021
WO WO2022109143 5/2022

OTHER PUBLICATIONS

U.S. Appl. No. 18/601,705, filed Mar. 11, 2024, Redford.
(Continued)

*Primary Examiner* — Chao Sheng
(74) *Attorney, Agent, or Firm* — HAYES SOLOWAY P.C.

(57) ABSTRACT

A non-occluded dual lumen endotracheal tube is disclosed that includes a first lumen for delivering oxygen or other gases to a patient, and a second lumen for suctioning secretions or other fluids from the patient's airway. The endotracheal tube also includes a fiber-optic imaging system and an AI hyperspectral imaging system for providing real-time, high-resolution images of the patient's airway. The AI hyperspectral imaging system is configured to analyze spectral characteristics of image pixels captured by the camera and to correct and enhance the images provided by the fiber-optic imaging system by reducing noise, correcting distortion and improving contrast and brightness, resulting in improved visualization of the patient's airway and better detection of abnormalities or other conditions.

7 Claims, 2 Drawing Sheets

(56) References Cited

U.S. PATENT DOCUMENTS

| | | | | |
|---|---|---|---|---|
| 2019/0298151 | A1 | 10/2019 | Frangioni | |
| 2021/0007585 | A1 | 1/2021 | Gill, IV et al. | |
| 2021/0369394 | A1 | 12/2021 | Braido et al. | |
| 2022/0086416 | A1 | 3/2022 | Liu | |
| 2022/0104713 | A1 | 4/2022 | Shelton, IV | |
| 2022/0183760 | A1 | 6/2022 | Fouts et al. | |
| 2022/0304626 | A1 | 9/2022 | Reiner | |
| 2022/0361738 | A1 | 11/2022 | Chen | |
| 2023/0125377 | A1* | 4/2023 | Gao | G01J 3/2823<br>356/326 |
| 2023/0342912 | A1 | 10/2023 | He et al. | |
| 2024/0280490 | A1 | 8/2024 | Perry et al. | |
| 2024/0298889 | A1 | 9/2024 | Joshi et al. | |

OTHER PUBLICATIONS

International Search Report and Written Opinion issued in PCT/US2024/019406, dated Jun. 25, 2024, 10 pages.

International Search Report and Written Opinion issued in PCT/US2024/019433, dated Jun. 18, 2024, 16 pages.

* cited by examiner

NON-OCCLUDED DUAL LUMEN ENDOTRACHEAL TUBE

CROSS REFERENCE TO RELATED APPLICATION

This application claims priority to U.S. Provisional Ser. No. 63/451,477, filed Mar. 10, 2023, the contents of which are incorporated herein in their entirety by reference.

FIELD OF THE INVENTION

The present disclosure relates to airway management devices, and more particularly to dual lumen endotracheal tubes including imaging systems, and will be described in connection with such utility, although other utilities are contemplated.

BACKGROUND AND SUMMARY

Endotracheal tubes are commonly used in medical procedures, such as mechanical ventilation and general anesthesia, to provide a secure airway for the patient. However, traditional endotracheal tubes can occlude the patient's airway, making it difficult to visualize the patient's airway and to suction secretions or other fluids from the airway.

In recent years, fiber-optic imaging systems have been developed that can provide real-time, high-resolution images of the patient's airway. However, these images can be distorted or degraded due to factors such as lighting conditions, patient motion, and ambient noise.

Artificial intelligence (AI) hyperspectral imaging systems also have been developed that can correct and enhance images by analyzing the spectral characteristics of the image pixels. However, these systems have not been widely used in conjunction with fiber-optic imaging systems in endotracheal tubes.

The present disclosure provides a non-occluded dual lumen endotracheal tube that includes a fiber-optic imaging system and an AI hyperspectral imaging system for providing real-time, high-resolution images of the patient's airway. The AI hyperspectral imaging system is configured to correct and enhance the images provided by the fiber-optic imaging system, resulting in improved visualization of the patient's airway and better detection of abnormalities or other conditions.

More particularly, in accordance with the present disclosure, we provide a non-occluded dual lumen endotracheal tube for a human or animal patient comprising: a first lumen configured for delivering oxygen or other gases to the patient; a second lumen configured for suctioning secretions or other fluids from the patient's airway; a fiber-optic imaging system comprising a fiber-optic cable having a distal end configured for insertion into the patient's airway, a light source configured for illuminating the patient's airway; and a camera configured for capturing images of the airway; and an Artificial Intelligence (AI) hyperspectral imaging system comprising a processor and a memory configured to analyze spectral characteristics of image pixels captured by the camera and to correct and enhance the images by reducing noise, correcting distortion, and improving contrast and brightness.

In one embodiment the non-occluded dual lumen endotracheal tube comprises a monitor for displaying the corrected and enhanced images.

In another embodiment the AI hyperspectral imaging system is programmed to detect abnormalities or other conditions in the patient's airway.

The present disclosure also provides a method for visualizing an airway of a human or animal patient, providing a non-occluded dual lumen endotracheal tube, comprising: a first lumen configured for delivering oxygen or other gases to the patient; a second lumen configured for suctioning secretions or other fluids from the patient's airway; a fiber-optic imaging system comprising a fiber-optic cable having a distal end configured for insertion into the patient's airway, a light source for illuminating the patient's airway, and a camera configured for capturing images of the airway; and an AI hyperspectral imaging system comprising a processor and a memory configured to analyze spectral characteristics of image pixels captured by the camera and to correct and enhance the images by reducing noise, correcting distortion, and improving contract and brightness; inserting a distal end of the endotracheal tube into the patient's airway; illuminating the patient's airway with the light source; capturing images of the airway with the camera; analyzing spectral characteristics of image pixels captured by the camera with the AI hyperspectral imaging system; correcting and enhancing the images with the AI hyperspectral imaging system by reducing noise, correcting distortion, and improving contrast and brightness; and displaying the corrected and enhanced images on a monitor.

In a further embodiment, the method comprises detecting abnormalities or other conditions in the patient's airway using corrected and enhanced images.

BRIEF DESCRIPTION OF THE DRAWINGS

Further features and advantages of the instant disclosure will be seen from the following detailed description, taken in conjunction with the accompanying drawing, wherein like numerals depict like parts; and wherein.

DETAILED DESCRIPTION

Figure 1:
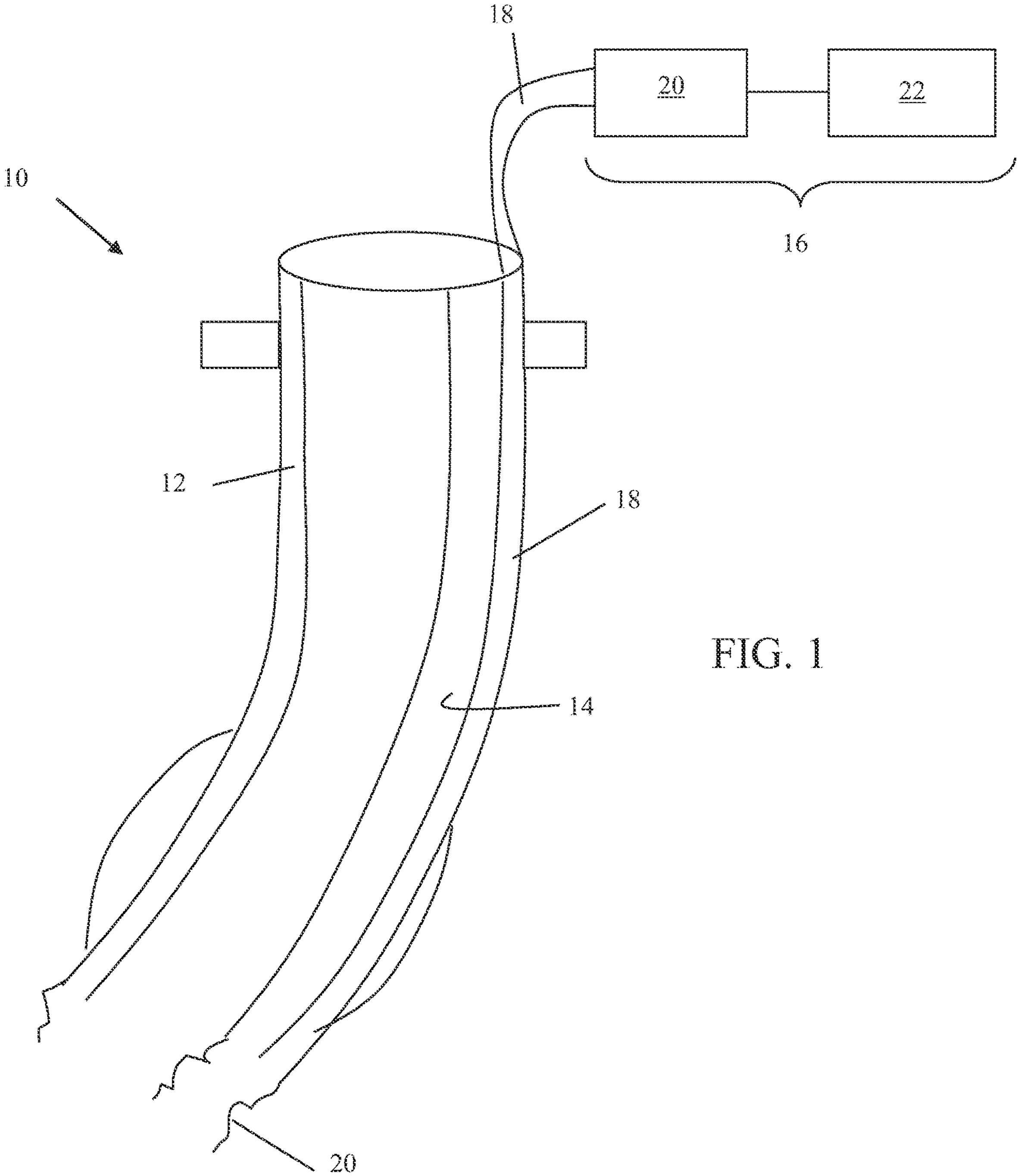
FIG. 1 is a schematic drawing of a dual-lumen endotracheal device in accordance with the present disclosure.

Referring to FIG. 1, a non-occluded dual lumen endotracheal device 10 in accordance with the present disclosure includes a first lumen 12 configured for delivering oxygen or other gases to a patient, and a second lumen 14 configured for suctioning secretions or other fluids from the patient's airway. The endotracheal device 10 also includes a fiber-optic imaging system 16 and an AI hyperspectral imaging system 50 (shown in FIG. 2) configured for providing real-time, high-resolution images of the patient's airway. The endotracheal device also may include a bite block, face mask, proximal cuff, and other structures common to endotracheal tubes, which have been omitted from the drawing figures as to not obscure the novel feature of the present disclosed endotracheal tube.

Fiber-optic imaging system 16 includes a fiber-optic cable 18 with a distal end 20 configured to be inserted into the patient's airway. The fiber-optic cable 18 is connected to a light source 20 and a camera 22, which are located outside the patient's body. The light source 20 is configured to illuminate the patient's airway, and the camera 22 is configured to capture images of the airway.

The AI hyperspectral imaging system 50 includes a processor 52 and a memory 54 that are configured to analyze the spectral characteristics of the image pixels captured by the camera 22. As will be described below AI hyperspectral imaging system 50 is programmed to correct and enhance the images by reducing noise, correcting distortion, and improving contrast and brightness.

Figure 2:
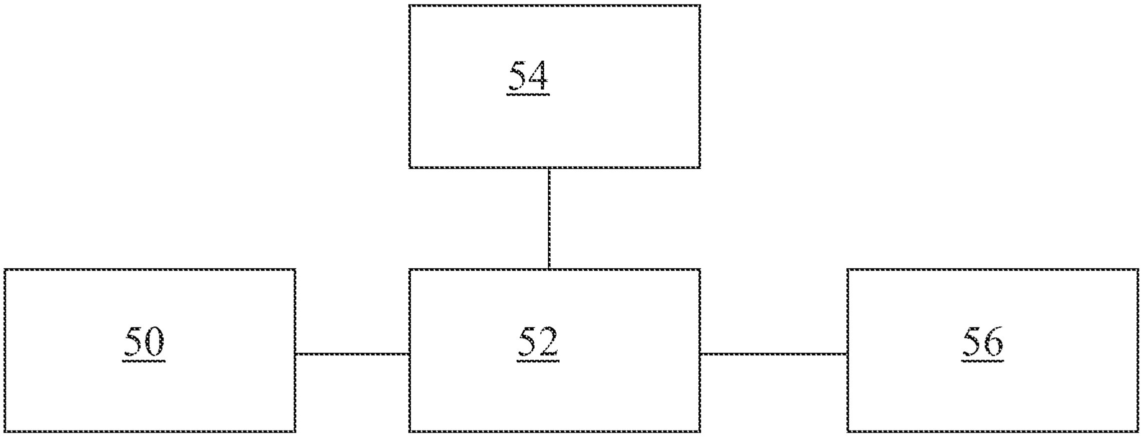
FIG. 2 is a flow chart depicting operation of an AI imaging system in accordance with the present disclosure.

Referring also to FIG. 2, the corrected and enhanced images are displayed on a monitor 56, which can be viewed by the healthcare provider. The healthcare provider can use the images to visualize the patient's airway and to detect abnormalities or other conditions, such as mucus plugs, foreign bodies, or inflammation.

The non-occluded design of the endotracheal tube 10 allows for continuous suctioning of secretions or other fluids from the patient's airway, while also providing a secure airway for the delivery of oxygen or other gases. This can help to prevent complications such as atelectasis, pneumonia, and respiratory failure.

Referring to FIG. 1, in use, the endotracheal device 10 is inserted into the patient's trachea through the mouth or the nose. The fiber-optic imaging system 16 is activated, and the AI hyperspectral imaging system 50 begins correcting and enhancing the images captured by the camera 22. The healthcare provider can view the corrected and enhanced images on the monitor and use them to guide the placement of the endotracheal device 10 and to monitor the patient's airway during the medical procedure.

The non-occluded dual lumen endotracheal device 10 with fiber-optic imaging system 16 and AI hyperspectral imaging correction and enhancements 50 has the advantage to improve patient outcomes by providing real-time, high-resolution images of the patient's airway and by correcting and enhancing these images to improve visualization and detection of abnormalities or other conditions.

To correct distortion in the images captured by the fiber-optic imaging system, the following equation is used:

corrected_image=distortion_correction_matrix*distorted_image where "corrected_image" is the corrected version of the distorted image, "distortion_correction_matrix" is a matrix containing the distortion correction parameters, and "distorted_image" is the original distorted image.

To improve the contrast and brightness of the images, the following equation is used:

enhanced_image=contrast_enhancement_factor*original_image+brightness_enhancement_factor where "enhanced_image" is the enhanced version of the original image, "contrast_enhancement_factor" is a scalar value representing the desired level of contrast enhancement, and "brightness_enhancement_factor" is a scalar value representing the desired level of brightness enhancement.

To detect abnormalities or other conditions in the patient's airway, the AI hyperspectral imaging system uses machine learning algorithms and statistical analysis to analyze the spectral characteristics of the image pixels. For example, the system uses a support vector machine (SVM) classifier to classify the pixels as normal or abnormal, based on a training dataset of known normal and abnormal pixels. The SVM classifier is trained using the following equation:

$$\text{minimize } (1/2) * \|w\|^\wedge 2 + C * \sum[i = 1 \text{ to } n](\xi[i]) \text{ subject to } y[i] * (w * x[i] + b) >= 1 - \xi[i],\ \xi[i] > = 0$$

where "w" and "b" are the weights and biases of the SVM classifier, "x" and "y" are the input features and labels of the training dataset, "C" is a regularization parameter, and "ξ" is the slack variable.

To reduce noise in the images, the AI hyperspectral imaging system uses image denoising techniques, such as non-local means denoising. This technique works by replacing each pixel in the image with the weighted average of pixels in a local neighborhood, where the weights are determined based on the similarity between the pixel and its neighbors. The denoised image is calculated using the following equation:

$$\text{denoised\_image}[i, j] = \sum[k = -R \text{ to } R, 1 = -R \text{ to } R] \text{ weights } [k, 1] * \text{original\_image}[i + kj + 1] / \sum[k = -R \text{ to } R, 1 = -R \text{ to } R] \text{ weights}[k, 1]$$

where "denoised_image" is the denoised version of the original image, "original_image" is the original noisy image, "weights" is the matrix of weights, "R" is the radius of the local neighborhood, and "i" and "j" are the row and column indices of the pixel being denoised.

To improve the accuracy of the AI hyperspectral imaging system's corrections and enhancements, the system uses iterative algorithms that refine the corrections and enhancements based on the error between the original and corrected/enhanced images. For example, the system uses the gradient descent algorithm to iteratively minimize the error between the original and corrected/enhanced images. The error is calculated using the mean squared error (MSE) between the two images, as follows:

$$\text{error} = 1/(n * m) * \sum[i = 1 \text{ to } n] \sum[j = 1 \text{ to } m](\text{original\_image}[i, j] - \text{corrected/enhanced\_image}[i, j])^\wedge 2$$

where "error" is the MSE between the original and corrected/enhanced images, "n" and "m" are the dimensions of the images, and "i" and "j" are the row and column indices of the pixel being compared. The corrected/enhanced image is then be updated using the following equation:

corrected/enhanced_image[*i,j*]=corrected/enhanced_image[*i,j*]−learning_rate*error*(original_image[*i,j*]−corrected/enhanced_image[*i,j*])

where "learning_rate" is a scalar value representing the step size of the gradient descent algorithm.

Topographical integration:

Three-dimensional (3D) reconstruction of the patient's airway is created as follows: The fiber-optic imaging system captures a series of 2D images of the patient's airway from different angles, and the AI hyperspectral imaging system uses these images to construct a 3D model of the airway. This 3D model is used to visualize the airway from different perspectives and to measure the dimensions and shape of the airway.

Surface rendering of the patient's airway: The AI hyperspectral imaging system processes the 2D images captured by the fiber-optic imaging system to create a surface rendering of the airway. This surface rendering is used to highlight the topographical features of the airway, such as the tracheal rings, bronchi, and alveoli.

Virtual endoscopy of the patient's airway: The AI hyperspectral imaging system processes the 2D images captured by the fiber-optic imaging system to create a virtual endoscopy of the airway. This virtual endoscopy is used to simulate the view of the airway that would be seen during a traditional endoscopy, allowing the healthcare provider to navigate through the airway and inspect it in detail.

Optical coherence tomography (OCT) of the patient's airway. Optical coherence tomography (OCT) is a non-invasive imaging technique that uses light waves to produce high-resolution images of the internal structure of tissues. OCT works by shining a light source into the tissue and measuring the interference of the light reflected from the tissue. The interference patterns are then used to calculate the distance to different layers in the tissue, which can be used to create a detailed cross-sectional image of the tissue: The fiber-optic imaging system is used to capture OCT images of the airway, which are created by measuring the interference of light reflected from the tissue. These OCT images is used to visualize the layers of the airway and to detect abnormalities or other conditions in the tissue.

OCT has several advantages over other imaging techniques, such as X-ray and ultrasound, including high resolution, non-ionizing radiation, and the ability to image deep tissue layers. OCT has been widely used in ophthalmology to visualize the retina and other eye structures, but it has also been used in other medical fields, such as cardiology, dermatology, and gastroenterology. In the context of the non-occluded dual lumen endotracheal tube with fiber-optic imaging and AI hyperspectral imaging correction and enhancements, OCT could be used to visualize the layers of the airway and to detect abnormalities or other conditions in the tissue. For example, OCT could be used to detect inflammation, edema, or mucus accumulation in the airway. To use OCT with the endotracheal tube, the fiber-optic imaging system could be equipped with an OCT probe that is inserted into the patient's airway. The OCT probe could include a light source and a detector that are used to capture the interference patterns of the light reflected from the tissue. The AI hyperspectral imaging system could then process the interference patterns to create the OCT images of the airway.

What is claimed:

1. A method for visualizing an airway of a human or animal patient, comprising:

providing a non-occluded dual lumen endotracheal tube comprising a first lumen configured for delivering oxygen or other gases to the patient; a second lumen configured for suctioning secretions or other fluids from the patient's airway; a fiber-optic imaging system comprising a fiber-optic cable having a distal end configured for insertion into the patient's airway, a light source configured for illuminating the patient's airway, and a camera configured for capturing images of the airway; and an AI hyperspectral imaging system comprising a processor and a memory configured to analyze spectral characteristics of image pixels captured by the camera and to correct and enhance the images by reducing noise, correcting distortion, and improving contrast and brightness;

inserting the distal end of the endotracheal tube into the patient's airway;

imaging internal structure of tissue structures within the patient's airway using optical coherence tomography (OCT) by illuminating tissue of the patient's airway with the light source;

capturing the images of the airway with the camera;

capturing and measuring interference patterns of light reflected from the illuminated tissue;

calculating a distance to different layers in the tissue based on the interference pattern using the AI hyperspectral imaging system;

correcting and enhancing the images with the AI hyperspectral imaging system by reducing noise, correcting distortion, and improving contrast and brightness; and displaying the corrected and enhanced images on a monitor.

2. The method of claim 1, further comprising detecting abnormalities or other conditions in the patient's airway using the corrected and enhanced images.

3. The method of claim 1, wherein distortion of the images captured are corrected using the following equation:

$$\text{corrected\_image}=\text{distortion\_correction\_matrix}*\text{distorted\_image}$$

where "corrected_image" is the corrected version of each of the images, "distortion_correction_matrix" is a matrix containing the distortion correction parameters, and "distorted_image" is the original version of each of the images.

4. The method of claim 1, wherein contrast and brightness of the images captured are improved using the following equation:

$$\text{enhanced\_image} = \text{contrast\_enhancement\_factor} * \text{original\_image} + \text{brightness\_enhancement\_factor}$$

where "enhanced_image" is the enhanced version of each of the images, "contrast enhancement_factor" is a scalar value representing the desired level of contrast enhancement, and "brightness_enhancement_factor" is a scalar value representing the desired level of brightness enhancement.

5. The method of claim 1, including the step of using a support vector machine (SVM) classifier to classify the image pixels as normal or abnormal, based on a training dataset of known normal and abnormal pixels, using the following equation:

$$\text{minimize}(1/2) * \|w\|\text{^}2 + C * \Sigma[i = 1 \text{ to } n](\xi[i])$$

$$\text{subject to } y[n] * (w * x[i] + b) >= 1 + \xi[i],\ \xi[i] >= 0$$

where "w" and "b" are the weights and biases of the SVM classifier, "x" and "y" are the input features and labels of the training dataset, "C" is a regularization parameter, and "ξ" is the slack variable.

6. The method of claim 1, wherein the AI hyperspectral imaging system is configured to reduce noise by replacing each pixels in the images with the weighted average of pixels in a local neighborhood, where the weights are determined based on the similarity between each pixel and its neighbors, and calculating denoised image using the following equation:

$$\text{denoised\_image}[i, j] = \Sigma[k = -R \text{ to } R, 1 = -R \text{ to } R]\ \text{weights}[k, l] * \text{original\_image}[i + k, j + 1] / \Sigma[k = -R \text{ to } R, 1 = -R \text{ to } R]\ \text{weights}[k, l]$$

where "denoised_image" is the noise reduced version of each of the images, "original_image" is the original version of each of the images, "weights" is the matrix of weights, "R" is the radius of the local neighborhood, and "i" and "j" are the row and column indices of the pixel being denoised.

7. The method of claim 1, further comprising using iterative algorithms to refine corrections and enhancements of the AI hyperspectral imaging system based on an error between the images and the corrected/enhanced images, by using a gradient descent algorithm to iteratively minimize the error between the images and the corrected/enhanced images, and calculating the error using the mean squared error (MSE) between the two corresponding images, as follows:

$$\text{error} = 1/(n*m)*\Sigma[i=1 \text{ to } n]\Sigma[j=1 \text{ to } m] (\text{original\_image}[i,j] - \text{corrected/enhanced\_image}[i,j])\text{^}2$$

where "error" is the MSE between the original and corrected/enhanced images, "n" and "m" are the dimensions of the images, and "i" and "j" are the row and column indices of the pixel being compared, and the corrected/enhanced image is then be updated using the following equation:

$$\text{corrected/enhanced\_image}[i,j]=\text{corrected/enhanced\_image}[i,j]-\text{learning\_rate}*\text{error}*(\text{original\_image}[i,j]-\text{corrected/enhanced\_image}[i,j])$$

where "learning_rate" is a scalar value representing the step size of the gradient descent algorithm.

* * * * *